United States Patent [19]

Scanlon

[11] Patent Number: 4,756,028
[45] Date of Patent: Jul. 12, 1988

[54] SOUND REDUCTION HEADSET
[76] Inventor: Thomas A. Scanlon, 40 Hawthorne Ave., Barrington, R.I. 02806
[21] Appl. No.: 4,891
[22] Filed: Jan. 20, 1987
[51] Int. Cl.$^4$ ............................................. A61F 11/02
[52] U.S. Cl. ........................................ 2/209; 379/430; 403/80
[58] Field of Search ..................... 2/209, 423; 379/430; 403/80, 59; 181/141, 211

[56] References Cited

U.S. PATENT DOCUMENTS

| | | | |
|---|---|---|---|
| 1,525,043 | 2/1925 | Primrose | 403/59 X |
| 3,356,797 | 12/1967 | Konzelmann et al. | 379/430 |
| 3,845,505 | 11/1974 | Davison et al. | 2/423 X |
| 4,209,264 | 6/1980 | Hellberg | 2/209 X |
| 4,347,631 | 9/1982 | Newcomb | 2/423 |

*Primary Examiner*—Peter Nerbun
*Attorney, Agent, or Firm*—Robert J. Doherty

[57] ABSTRACT

An adjustable connector for connecting cups of a sound reduction headset to a headband. The connector includes an elastomeric slide that frictionally is held to the inner of two parallel end panels forming the terminal end portions of the headband. The outer panel shields the inner panel from the wearer's hair and thus serves to prevent the hair from catching in the slide's operation.

4 Claims, 1 Drawing Sheet

SOUND REDUCTION HEADSET

BACKGROUND AND OBJECTS OF THE INVENTION

This invention relates to a sound reduction headset and more particularly to an improved combination adjustment and connector device whereby the acoustical cups of such may be attached to the headband or other supporting element.

Headsets of this type are generally utilized in various work or recreational environments where it is desirable to reduce the sound entering one's ears. The normal headset includes a pair of accustical cups which at least partially encircle or surround one's ears and supporting mechanisms whereby the acoustical cups may be maintained in the desired position such as a headband which encircles the wearer's head or a helmet or work hat from which a supporting member extends so as to attach the cups in the desired position. As used herein, the term headband includes not only the normal structure in the form of a somewhat semi-circular or C-shaped element but also structures which include an intermediate work hat or helmet from which elements which ultimately position the acoustical cups depend.

A recurrent problem with such headsets is that the mechanisms utilized to obtain vertical adjustment of the acoustical cups so as to enable the headset to fit various sized and shaped heads of people is that the wearer's hair when worn long can contact such mechanisms and not only interfere with their operation but also catch one's hair and cause irritation or pain. In addition, sometimes it is sometimes necessary to remove the head gear quickly, and should one's hair be caught in the adjustment mechanism, such would present difficulty in achieving such result.

It is, accordingly, an object of the present invention to present a sound reduction headset of the above generally described type which includes a combination adjustable connector means whereby the cups may be connected and supported for easy adjustment with respect to the wearer's ears and head yet be constructed in such a manner that the wearer's hair is not normally contacted or caught in the operational mechanism of such improved adjustable connector means.

A further object of the present invention is the provision of an improved sound reduction headset which achieves the immediately aforesaid goal yet is of simple, relatively low cost construction, and easily operable.

These and other objects of the present invention are accomplished by providing a sound reduction headset of the type having a flexible headband adapted to overlie the wearer's head and terminating in ends adapted for disposition opposite the wearer's ears and wherein each end is in turn provided with an acoustical cup attached thereto for generally swivable movement with its respective end and adapted to at least partially enclose the wearer's ear; the improvement comprising an adjustable connector means for connecting the cups to their respective headband ends, said connector means including a longitudinally oriented outer end panel essentially forming the terminal end portion of each headband end and a longitudinally oriented inner end panel inwardly disposed from the generally parallel to said outer panel, and a slide member attached to said inner end panel and adapted for vertical adjustable movement thereon, said slide member having a body in contact with an inner surface of said inner end panel and from which a connector element inwardly extends for attaching said cup to said adjustable connector means, said inner panel of a lateral extent materially less than that of said outer end panel such that the outer end panel essentially shields said connector means from contact with the wearer's hair that may contact and overlie the outside surface of said outer end panel.

Other objects, features and advantages of the invention shall become apparent as the description thereof proceeds when considered in connection with the accompanying illustrative drawing.

DESCRIPTION OF THE DRAWING

In the drawing which illustrates the best mode presently comtemplated for carrying out the present invention.

DESCRIPTION OF THE PREFERRED EMBODIMENT

Figure 1:
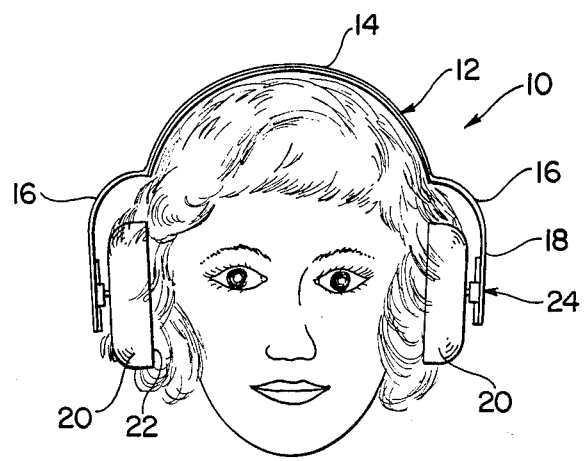
FIG. 1 is an elevational view showing a sound reduction headset incorporating the present invention positioned upon a wearer with long hair.

Turning now to the drawing and particularly FIG. 1, a sound reduction headset 10 in which the invention is utilized is shown in place upon a human wearer. Such headset 10 includes a headband 12 having a first portion 14 which partially encircles the head and is supported thereon and a pair of side extensions 16 downwardly dependent therefrom. The overall construction of the band 14 is semi-circular or C-shaped and includes opposed terminal end portions 18 to which acoustical cups 20 are positioned for both vertical adjustment with respect to the band 14 and for relative rotation therewith such that the cups may be comfortably and properly positioned so as to envelop the ears of the wearer and thus provide the desired sound protection.

It should also be pointed out that the present invention as will hereinafter be more fully explained may also relate to a sound producing device such as a radio in which the acoustical cups 20 are provided with sound but the overall nature of the device is still that of protecting the ear from unwanted sounds from the surrounding environment. Thus the term "sound reduction headset" refers to device which accomplish such overall objectives regardless of their specific purpose.

Generally the band 14 is formed as by injection molding from a stiff yet flexible plastic material and the ends 16 thereof outwardly flex from a more inward normal position to the position shown in FIG. 1 such that a modest inward force is applied to the cups 20 so that they are maintained in an effectively firm relationship to the sides of the wearer's head. Also the cups 20 are normally provided with an interior lining 22 formed from a soft compressible material such as foam rubber to better seal the ear from outside sound. As previously indicated, the band portion of the headband may also take the form of a helmet, work hat, or other intermediate member from which the side extensions 16 depend.

Figure 2:
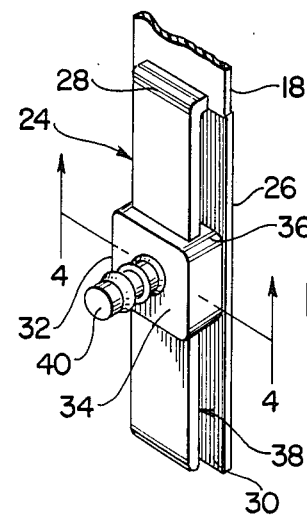
FIG. 2 is a partial perspective view of one of the end portions of the headband of FIG. 1 with the acoustical cup removed for clarity.
Figure 3:
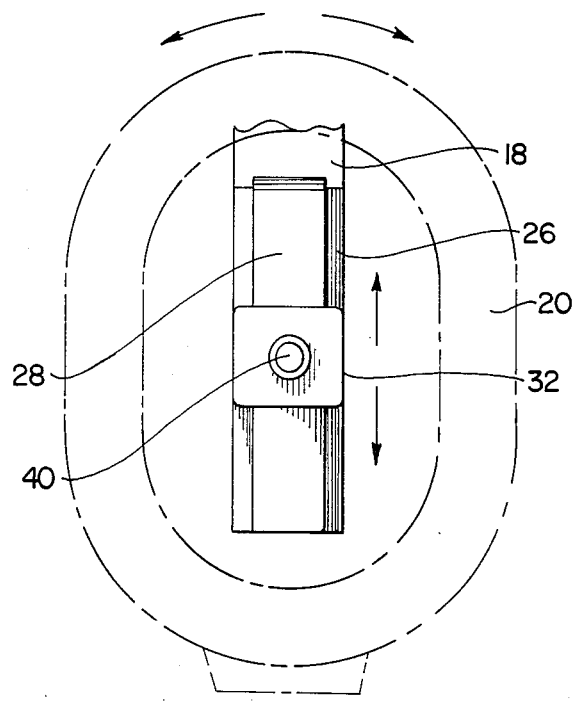
FIG. 3 is an elevational view taken from the inside of the headband portion shown in FIG. 2 on an enlarged scale and showing the acoustical cup in dotted lines.
Figure 4:
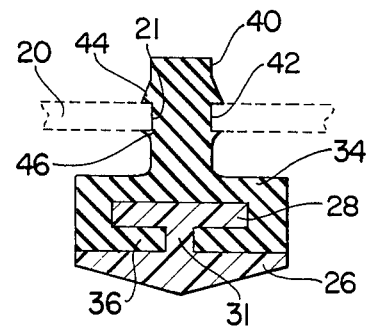
FIG. 4 is a cross-sectional view taken along the line 4—4 of FIG. 2 and shows in particular the manner in which the slide engages the inner panel portion of the headband end shown in FIG. 2.

The adjustable connector means 24 which is the subject matter of the present invention is best shown by reference to FIG. 2 in which it may be seen that an outer generally flat panel 26 forms an extension or terminal end portion of the headband ends 18. An inner panel 28 is disposed parallel to and inwardly of the inner surface 30 of the outer panel 26 and connected thereto by means of an intermediate web 31 preferably extending along the entire longitudinal extent of the inner panel 28 to provide rigidity thereto. A slide 32, as hereinafter will be more fully explained, is moved upwardly and downwardly on the panel 28 to provide for vertical adjustment of the cups 20.

The inner panel 28 is generally flat and is of a lateral extent materially less than that of the outer panel 26 and is generally centrally positoned with respect to the outer panel. Such positioning and extent, in effect, shields the inner panel 28 from contact with the wearer's hair. Most adjustment and acoustical cup supporting mechanisms would be positioned on the outer panel 26 and thus be able to catch the wearer's hair or otherwise interfere with the operation of the adjustment and supporting device. In the present device, not only is the inner panel 28 inwardly positoned with respect to the outer panel 26 but it is also of a substantially lesser width so as to provide for protected or sheltered positioning of the slide 32 in the intended manner so as to reduce or eliminate undesirable contact with the slide from the wearer's hair.

Such slid 32 includes a body 34 and a pair of inwardly extending opposed fingers 36 which are adapted to extend into a pair of slots 38 cooperatively formed by the outer surface of the inner panel 28, the web 31, and the inner surface of the outer panel 26. The slide 32 is formed from a hard, yet flexible, elastomeric material such as rubber but is dimensioned so as to rather tightly fit the inner panel 26 so as to partially envelop such and provide the necessary friction such that the slide must be forcibly moved from one position to the another. In this way then placement of the slide 32 with respect to the inner panel 28 vertically positions the cups 20 in the desired height relationship and such relationship is assuredly maintained by the aforesaid frictional forces.

The slide 32 also includes a connector element 40 in the form of a post which inwardly upwardly extends from the body 34 and is provided with a circular recess 42 in which the edges of an opening 21 formed in the outer shell of the acoustical cup are adapted to extend and thus form the connection between the slide 32 and the cups 20. A lead in ramp 44 as well as a shelf 46 may be provided on opposite sides of the recess 42 to facilitate such action. It should be thus clear that the cup is not only vertically adjustable with respect to the terminal portion of the headband 18 by reason of its attachment to the slide 32 but it is also rotationally adjustable thereto because of the aforementioned connection between the opening 21 and the recess 42. Accordingly, a usable yet simply constructed connector device has been provided such that the desired attachment of acoustical cups to the headband of sound reduction headsets may be provided while simultaneously reducing or eliminating the problem of having the wearer's hair catching therein or otherwise interfere with the desired objects of the present invention.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. In a sound reduction headset of the type having a flexible headband adapted to overlie the wearer's head and terminating in ends adapted for disposition opposite the wearer's ears and each such end in turn provided with an acoustical cup attached thereto and having generally rotational movement with respect to the end to which it is attached and adapted to at least partially enclose the wearer's ear; the improvement comprising, an adjustable connector means for connecting the cups to the headband ends to which they are respectively attached, said connector means including a longitudinally oriented outer end panel essentially forming the terminal end portion of each headband end and a longitudinally oriented inner end panel inwardly disposed from and generally parallel to said outer panel, and a slide member attached to said inner end panel, and adapted for vertical adjustable movement thereon, said slide member having a body in contact with an inner surface of said inner end panel and from which a connector element inwardly extends for attaching said cup to said adjustable connector means, said inner panel having a lateral extent materially less than that of said outer end panel such that the outer end panel essentially shields said connector means from contact with the wearer's hair that may contact and overlie the outside surface of said outer end panel.

2. The improved sound reduction headset of claim 1, said inner panel generally centrally superposed with relation to said panel panel.

3. The improved sound reduction headset of claim 2, including a longitudinal web disposed between said inner and outer panels and rigidly connecting said panels together, said web and said panels forming a pair of longitudinally extending slots between said panels, said slide having a pair of laterally opposed fingers forwardly disposed from said slide body and adapted to at least partially surround said inner panel by extending into said slots.

4. The improved sound reduction headset of claim 3, said slide being formed of a rigid, high friction elastomeric material such that it requires forcible movement for repositioning on said inner panel.

* * * * *